United States Patent

Fukumoto et al.

Patent Number: 5,621,146
Date of Patent: Apr. 15, 1997

[54] PROCESS FOR PRODUCING 2,4-DIHYDROXYACETOPHENONE

[75] Inventors: Takashi Fukumoto; Katsuji Ujita; Toshiki Mori, all of Nakajo-machi; Kozo Nakao, Yokohama; Yoshin Tamai, Shibata, all of Japan

[73] Assignee: Kuraray Co., Ltd., Kurashiki, Japan

[21] Appl. No.: 568,485

[22] Filed: Dec. 7, 1995

[30] Foreign Application Priority Data

Dec. 7, 1994 [JP] Japan .................................. 6-330744

[51] Int. Cl.$^6$ .................................................. C07C 45/45
[52] U.S. Cl. ............................................ 568/319; 568/322
[58] Field of Search ................................. 568/319, 322, 568/323

[56] References Cited

PUBLICATIONS

Database WPI, Derwent Publications, AN–86–248732/38, JP–A–61–176548, Aug. 8, 1986.
Database WPI, Derwent Publications, AN–84–130435/21, JP–A–59–65039, Apr. 13, 1984.
Database WPI, Derwent Publications, AN–86–254400/39, JP–A–61–180738, Aug. 13, 1986.
Database WPI, Derwent Publications, AN–90–056198/08, JP–A–2–011536, Jan. 16, 1990.
Database WPI, Derwent Publications, AN–86–025604/04, JP–A–60–248642, Dec. 9, 1985.

*Primary Examiner*—James H. Reamer
*Attorney, Agent, or Firm*—Oblon, Spivak, McClelland, Maier & Neustadt, P.C.

[57] ABSTRACT

A process for producing 2,4-dihydroxyacetophenone is provided wherein resorcinol and acetic acid are reacted in the presence of a proton acid catalyst while removing formed water.

10 Claims, No Drawings

PROCESS FOR PRODUCING 2,4-DIHYDROXYACETOPHENONE

BACKGROUND OF THE INVENTION

1. Field of the Invention

The present invention relates to a process for producing 2,4-dihydroxyacetophenone. The 2,4-dihydroxyacetophenone obtained by the present invention is useful both as an intermediate for producing 2,4-dihydroxy-3-propylacetophenone which is a starting material for medicines to treat allergic diseases and as a starting material for photosensitive materials and anti-suntan cosmetics.

2. Related Art of the Invention

Many processes have been reported for producing 2,4-dihydroxyacetophenone. Typical processes include, for example:

(1) processes wherein resorcinol and acetic acid are reacted in the presence of zinc chloride (see Japanese Patent Laid-open Nos. Sho 61-176548 and Sho 59-65039, and Organic Synthesis Coll., Vol. III, page 761);

(2) a process wherein resorcinol and acetyl chloride are reacted in the presence of zinc chloride (see Japanese Patent Laid-open No. Sho 61-180738);

(3) a process wherein resorcinol and acetic anhydride are reacted in the presence of zinc chloride (see Japanese Patent Laid-open No. Hei 2-11536);

(4) a process wherein resorcinol and acetic anhydride are reacted in the presence of aluminum chloride (see RO 53277 (Rumanian Patent)); and (5) processes wherein resorcinol and acetic anhydride are reacted in the presence of sulfuric acid (see J. S. African Chem. Inst. 26, 41 (1943) and Japanese Patent Laid-open No. Sho 60-248642).

However, these processes have several problems to be solved when carried out on an industrial scale. More particularly, the processes (1) to (4) mentioned above need to use Lewis acids, such as zinc chloride and aluminum chloride, in stoichiometric amounts relative to resorcinol. Therefore, in order to put the processes into practice on an industrial scale, it is necessary to use, in large amounts, these Lewis acids unstable in the presence of water. In addition, these processes involve a problem on the treatment of waste water, because the Lewis acids are a kind of metal-containing catalyst. Further, the processes (2) to (5) are disadvantageous in that these processes need to use chemicals, such as acetyl chloride and acetic anhydride, unstable in the presence of water and difficult to handle. With the process (5), it has also been pointed out that the obtained 2,4-dihydroxyacetophenone is highly colored.

In view of the above facts, the known processes for producing 2,4-dihydroxyacetophenone are not suitable for industrial applications.

SUMMARY OF THE INVENTION

It is an object of the present invention to provide an industrially useful process for producing 2,4-dihydroxyacetophenone in an easy and simple manner.

The object of the present invention can be achieved by a process described hereinbelow. More particularly, the present invention provides a process for producing 2,4-dihydroxyacetophenone, wherein resorcinol and acetic acid are reacted in the presence of a proton acid catalyst while removing the formed water.

DETAILED DESCRIPTION OF THE INVENTION

The present invention is described in more detail.

The reaction of resorcinol and acetic acid according to the present invention proceeds as shown in the following scheme, wherein the phenolic hydroxy group of resorcinol is initially acetylated, followed by the Fries-rearrangement of the acetyl group to give 2,4-dihydroxyacetophenone.

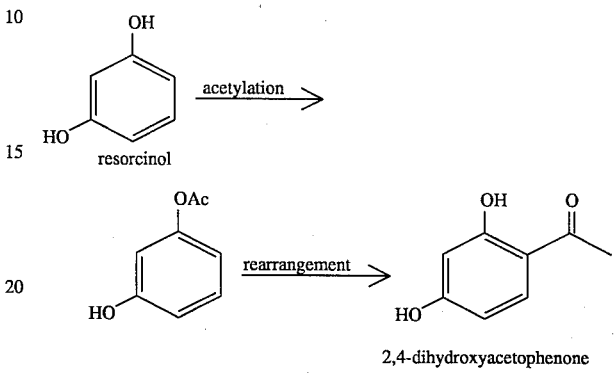

2,4-dihydroxyacetophenone

As will be apparent from the above reaction scheme, the process of the present invention essentially differs from the known processes of producing 2,4-dihydroxyacetophenone. In the known processes, so-called Friedel-Crafts acylation is employed wherein the acetyl group is introduced into the aromatic ring of resorcinol only by one step with acetic acid, acetyl chloride, acetic anhydride or the like in the presence of a Lewis acid such as zinc chloride or aluminum chloride.

The proton acid catalyst used in the present invention acts to promote both the acetylation of the phenolic hydroxy group and the Fries-rearrangement of the acetyl group in the above reaction scheme. Examples of such proton acid catalyst include mineral acids such as sulfuric acid, hydrochloric acid and polyphosphoric acid, organic sulfonic acids such as p-toluenesulfonic acid, methanesulfonic acid and camphorsulfonic acid, and strongly acidic ion-exchange resins including those ion-exchange resins having sulfonic acid group such as Amberlyst 15 and Amberlyst 16 (both made by Rohm & Haas, CO., LTD.), Dowex Marathon C (made by Dow Chemical Co.), Didion SK-1B (H-type) (made by Mitsubishi Chemical Corporation).

These proton acid catalysts can be used singly or in combination.

Where mineral acids or organic sulfonic acids are used as a proton acid catalyst, the amount of the proton acid catalyst generally ranges from 0.0001 to 1 mole per mole of resorcinol. In view of the reaction time and the cost of production, it is preferred to use the proton acid catalyst within a range of 0.001 to 0.1 mole per mole of resorcinol.

On the other hand, when the strongly acidic ion-exchange resin is used as the proton acid catalyst, it is generally employed in an amount of 0.1 wt % to 2 times by weight of resorcinol. From the standpoint of the reaction time and the cost of production, the amount of the proton acid catalyst is preferably within a range of 1 to 10 wt % of the resorcinol.

In the practice of the present invention, it is preferred that the strongly acidic ion-exchange resin is used as the proton acid catalyst so that the coloration of 2,4-dihydroxyacetophenone is effectively decreased.

The amount of acetic acid used in the present invention is generally in the range of 0.5 to 100 moles per mole of resorcinol. It is preferred from the standpoint of the reaction time and the cost of production that the amount of the acetic acid ranges from 1 to 8 moles per mole of resorcinol.

In order to make the reaction proceed effectively, the reaction should be carried out while removing the formed water by means of distillation or the like. If the formed water is not removed in the course of the reaction, a high conversion of resorcinol cannot be achieved as will become apparent from Comparative Example 1 appearing hereinafter.

In the practice of the present invention, the formed water can be distilled off from the reaction system in the form of a mixture with acetic acid. In this case, if necessary, supplemental acetic acid can be added to the reaction system. Alternatively, the formed water can be distilled off from the reaction system using co-solvent. Such co-solvents preferably include organic solvents separable into two layers when mixed with water. Examples of co-solvent include ether solvents such as diisopropyl ether and dibutyl ether, ester solvents such as ethyl acetate and butyl acetate, aromatic hydrocarbon solvents such as toluene and benzene, and aliphatic hydrocarbon solvents such as hexane and heptane. Of these, diisopropyl ether and ethyl acetate are preferred. These co-solvents can be used singly or in combination.

The amount of the co-solvent is not critical, and is generally within a range of 0.01 to 100 times by weight of resorcinol.

Still alternatively, the formed water can also be removed by use of dehydrating agents such as anhydrous magnesium sulfate and molecular sieves.

The reaction of resorcinol and acetic acid according to the present invention is conducted generally at a temperature of from 50° to 200° C., preferably from 80° to 130° C. The reaction time is generally within a range of from 30 minutes to 30 hours.

The isolation of 2,4-dihydroxyacetophenone from the reaction mixture can be carried out by any known procedures. In the practice of the present invention, it is preferred to isolate the product in the following manner.

The reaction mixture is first concentrated. Then, water containing 0.01 to 32 wt % of a mineral acid such as sulfuric acid or hydrochloric acid or such a strongly acidic ion-exchange resin as set out hereinbefore is added to the concentrate, followed by maintaining the mixture at a temperature ranging from 10° C. to a refluxing temperature within a range of time of from 10 minutes to 20 hours. The obtained solution is cooled down to a temperature ranging from room temperature to −10° C. The precipitated 2,4-dihydroxyacetophenone is collected through filtration using a glass filter, a paper filter or cloth filter. If a solid acid such as an acidic ion-exchange resin is employed as the proton acid catalyst, the solid acid is preferably separated from the reaction mixture such as by filtration prior to the concentration of the reaction mixture. The water is preferably added in amounts of 1 to 200 times by weight of resorcinol.

According to the present invention, 2,4-dihydroxyacetophenone can be produced in an easy and simple manner, with the result of the low cost of the production. The process of the present invention does not use any metal-containing catalyst, which is the cause of the problem of treatment of waste water, or acetyl chloride or acetic anhydride, which is unstable in the presence of water and difficult to handle. So, the process of the present invention is very useful as a process for producing 2,4-dihydroxyacetophenone on an industrial scale.

Other features of the present invention will become apparent in the course of the following descriptions of exemplary embodiments which are given for illustration of the present invention and are not intended to be limiting thereof.

EXAMPLES

Example 1

110 g (1 mol) of resorcinol, 440 g (7.3 mol) of acetic acid, 16 g of diisopropyl ether and 5.5 g of Amberlyst 15 (strongly acidic ion-exchange resin) were charged into a 500 ml three-necked flask equipped with a thermometer and also with a distillation column having a Dean-Stark trap (water separator) and a reflux condenser, followed by heating to an inner temperature of 124° C. While discharging water distilled off from the Dean-Stark trap, the reaction of resorcinol and acetic acid was continued at the temperature for 10 hours.

The reaction mixture was cooled down to room temperature, then the strongly acidic ion-exchange resin was removed by filtration. The filtrate was subjected to distillation under reduced pressure to remove about 380 g of the acetic acid and diisopropyl ether. 640 g of water containing 1.3 g (0.013 mol) of sulfuric acid was added to the residue, and the mixture was refluxed for 6 hours to give a homogeneous solution. The thus obtained solution was cooled down to room temperature and the precipitates were collected to give 109 g (0.72 mol) of 2,4-dihydroxyacetophenone (melting point: 144.8° to 145.5° C., yield: 72%). The analysis of the 2,4-dihydroxyacetophenone through gas chromatography revealed that the purity of the product was 99.3%.

Analysis conditions of gas chromatography (GC-8A, made by Shimadzu Corporation)

Column: Thermon 1000+H3PO4 5+0.5% Chromosorb W (AW-DMCS) 1m

Temperature: Injection temperature of 230° C., heated from an initial temperature of 100° C. to a final temperature of 190° C. at a rate of 10° C./minute.

Detector: FID detector, temperature: 230° C.

Internal standard: Biphenyl

The NMR data of the 2,4-dihydroxyacetophenone are as follows.

$^1$H-NMR: 300 MHz (CDCl$_3$, δ: ppm)

12.68 (1H, s), 9.92 (1H, s), 7.58 (1H, d, J=8.7 Hz), 6.39 (1H, d, J=8.7 Hz), 6.37 (1H, s), 2.52 (3H, s)

In order to assess the degree of coloration of the product, 0.25 g of the 2,4-dihydroxyacetophenone obtained above was dissolved in 5 ml of ethanol (concentration of 2,4-dihydroxyacetophenone: 50 g/liter), followed by measurement of a transmittance to visible light whose wavelength was 485 nm, with the result of 84.7% of transmittance.

Example 2

110 g (1 mol) of resorcinol, 222 g (3.7 mol) of acetic acid and 5.5 g of Amberlyst 15 (strongly acidic ion-exchange resin) were charged into a reactor as used in Example 1 and heated to an inner temperature of 124° C. While fractions of not higher than 110° C. were distilled off from the top of the distillation column and a corresponding amount of fresh acetic acid was added to the reaction mixture, the reaction of resorcinol and acetic acid was continued for 15 hours. The fractions distilled off were found to be 150 g by weight.

The reaction mixture was cooled down to room temperature, then the strongly acidic ion-exchange resin was removed by filtration. About 80 g of the acetic acid was distilled off from the filtrate under reduced pressure. 640 g of water containing 1.3 g (0.013 mol) of sulfuric acid was added to the residue, and the mixture was refluxed for 6 hours to give a homogeneous solution. The thus obtained solution was cooled down to room temperature, and the precipitates were collected to give 106 g (0.70 mol) of 2,4-dihydroxyacetophenone with a purity of 99.7% (yield: 70%).

Example 3

11 g (0.1 mol) of resorcinol, 44 g (0.7 mol) of acetic acid, 0.1 g (0.001 mol) of sulfuric acid and 3 g of diisopropyl ether were charged into a 100 ml three-necked flask equipped with a thermometer and also with a distillation column having a Dean-Stark trap (water separator) and a reflux condenser, followed by heating to an inner temperature of 124° C. While discharging water distilled off from the Dean-Stark trap, the reaction of resorcinol and acetic acid was continued for 6 hours.

About 30 g of the acetic acid was distilled off from the reaction mixture under reduced pressure. 64 g of water was added to the residue, and the mixture was refluxed for 6 hours to give a homogeneous solution. The thus obtained solution was cooled down to room temperature, and the precipitates were collected to give 9 g (0.6 mol) of 2,4-dihydroxyacetophenone with a purity of 99.1% (yield: 60%).

Example 4

The general procedure of Example 3 was repeated except that 0.9 g (0.005 mol) of p-toluenesulfonic acid monohydrate was used in place of sulfuric acid, to give 9.4 g (0.62 mol) of 2,4-dihydroxyacetophenone with a purity of 99.2% (yield: 62%).

Comparative Example 1

11 g (0.1 mol) of resorcinol, 22 g (0.37 mol) of acetic acid and 0.55 g of Amberlyst 15 (strongly acidic ion-exchange resin) were charged into a 100 ml three-necked flask equipped with a thermometer and a reflux condenser, followed by heating to an inner temperature of 124° C., at which the reaction of resorcinol and acetic acid was continued for 15 hours. The reaction mixture was analyzed through gas chromatography, revealing that the reaction mixture contained 5.2 g of resorcinol, 7.3 g of 2,4-dihydroxyacetophenone and 0.5 g of resorcinol monoacetate. The conversion of the resorcinol was found to be 52.7%.

Comparative Example 2

55 g (0.5 mol) of resorcinol and 60 g (1 mol) of acetic acid were charged into a 500 ml three-necked flask equipped with a thermometer and a dropping funnel, followed by heating to an inner temperature of 70° to 75° C. At the temperature, 51 g (0.5 mol) of acetic anhydride was added dropwise to the solution in 1 hour. The mixture was stirred for 30 minutes at the same temperature.

The reaction mixture was heated to 95° C., at which the acetic acid was distilled off under reduced pressure. Thereafter, the temperature of the solution was raised to 124° C., to which 1.1 g of concentrated sulfuric acid was added and the mixture was stirred for 75 minutes. 330 g of water was added to the reaction mixture, followed by heating to 90° C. or above to give homogeneous solution. The solution was cooled down to room temperature, and the precipitates were collected to give 51.66 g of 2,4-dihydroxyacetophenone with a purity of 93% (yields 68%).

0.25 g of the 2,4-dihydroxyacetophenone was dissolved in 50 ml of ethanol (concentration of 2,4-dihydroxyacetophenone: 5 g/liter), followed by measurement of a transmittance to visible light of 485 nm in wavelength, with the result of 0% of transmittance. The ethanol solution of the 2,4-dihydroxyacetophenone was diluted to ten times by volume with ethanol (concentration of 2,4-dihydroxyacetophenone: 0.5 g/liter), followed by further measurement of a transmittance to visible light of 485 nm in wavelength, with the result of 34.4% of transmittance.

Obviously, numerous modifications and variations are possible in light of the above teachings. It is therefore to be understood that within the scope of the appended claims the present invention may be practiced otherwise than as specifically described herein.

What is claimed is:

1. A process for producing 2,4-dihydroxyacetophenone, comprising:

reacting resorcinol and acetic acid in a reaction medium containing a proton acid catalyst, and removing water as it is formed by the reaction of resorcinol with acetic acid.

2. The process of claim 1, wherein said proton acid catalyst is at least one member selected from the group consisting of sulfuric acid, hydrochloric acid, polyphosphoric acid, p-toluenesulfonic acid, methanesulfonic acid, camphorsulfonic acid and strongly acidic ion-exchange resins.

3. The process of claim 1, wherein said proton acid catalyst consists of a strongly acidic ion-exchange resin.

4. The process of claim 1, wherein said acid catalyst is a mineral acid or organic sulfonic acid which is employed in an amount ranging from 0.0001 to 1 mol per mol of resorcinol.

5. The process of claim 3, wherein said strongly acidic ion-exchange resin catalyst is employed in an amount of 0.1 weight % to 2 times by weight the amount of resorcinol.

6. The process of claim 1, wherein the amount of acetic acid in the reaction medium ranges from 0.5 to 100 mols per mol of resorcinol.

7. The process of claim 1, wherein said reaction medium contains a co-solvent.

8. The process of claim 7, wherein said co-solvent is an ether, an ester, an aromatic hydrocarbon or an aliphatic hydrocarbon.

9. The process of claim 7, wherein the amount of co-solvent ranges from 0.01 to 100 times by weight the amount of resorcinol.

10. The process of claim 1, which is conducted at a temperature ranging from 50° to 200° C.

* * * * *